(12) United States Patent
Wilmot et al.

(10) Patent No.: US 6,953,445 B2
(45) Date of Patent: Oct. 11, 2005

(54) WET/DRY AUTOMATIC INJECTOR ASSEMBLY

(75) Inventors: John G. Wilmot, Mount Airy, MD (US); Robert L. Hill, Abingdon, MD (US); John Whittier, Columbia, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 0 days.

(21) Appl. No.: 09/971,768

(22) Filed: Oct. 9, 2001

(65) Prior Publication Data

US 2002/0042592 A1 Apr. 11, 2002

Related U.S. Application Data

(60) Provisional application No. 60/238,448, filed on Oct. 10, 2000.

(51) Int. Cl.$^7$ .......................... A61M 37/00; A61M 5/00
(52) U.S. Cl. .......................................... 604/89; 604/190
(58) Field of Search ............................. 604/82–92, 416, 604/236, 218, 187, 190, 191

(56) References Cited

U.S. PATENT DOCUMENTS

| | | | | |
|---|---|---|---|---|
| 3,659,749 A | * | 5/1972 | Schwartz | 604/87 |
| 3,756,390 A | * | 9/1973 | Abbey et al. | 604/87 |
| 3,757,779 A | * | 9/1973 | Rovinski | 604/190 |
| 4,043,335 A | | 8/1977 | Ishikawa | |
| 4,306,554 A | | 12/1981 | Schwartz et al. | |
| 4,529,403 A | | 7/1985 | Kamstra | |
| 4,573,971 A | * | 3/1986 | Kamstra | 604/191 |
| 4,599,082 A | | 7/1986 | Grimard | |
| 4,643,721 A | * | 2/1987 | Brunet | 604/191 |
| 4,820,286 A | * | 4/1989 | van der Wal | 604/89 |
| 4,898,580 A | * | 2/1990 | Crowley | 604/90 |
| 5,531,683 A | * | 7/1996 | Kriesel et al. | 604/89 |
| 5,605,542 A | * | 2/1997 | Tanaka et al. | 604/89 |
| 5,704,918 A | | 1/1998 | Higashikawa | |

FOREIGN PATENT DOCUMENTS

| | | |
|---|---|---|
| EP | 0 361 668 | 4/1990 |
| EP | 0 405 320 A2 | 1/1991 |
| FR | 2 604 363 | 4/1988 |
| FR | 2 741 810 | 6/1997 |
| WO | WO96/01135 | 1/1996 |
| WO | WO01/93925 | 12/2001 |

OTHER PUBLICATIONS

A copy of the PCT Search Report dated May 3, 2002, issued in related PCT Application No. PCT/US01/42593.
A copy of the PCT Search Report dated May 3, 2002, issued in the corresponding PCT Application No. PCT/US01/42594.
A copy of the PCT Search Report dated May 3, 2002, issued in related PCT Application No. PCT/US01/42595.

* cited by examiner

*Primary Examiner*—Nicholas D. Lucchesi
*Assistant Examiner*—Matthew F DeSanto

(57) ABSTRACT

The present invention is directed to an automatic injection device containing a pre-loaded charge of medicament for automatically self-administering the medicament upon actuation thereof. The automatic injection device includes a housing assembly having an interior chamber, an activation assembly and a needle assembly for dispensing a dissolved medicament to a user. A dry compartment for storing a predetermined dry charge of dry medicament is located within the interior chamber. A wet compartment for storing a predetermined amount of liquid injection solution is also located within the interior chamber. A separation assembly separates the dry compartment from the wet compartment. The separation assembly prevents transfer of the liquid injection solution from the wet compartment to the dry compartment prior to activation of the automatic injection device. One or more medicament support assemblies located within the dry compartment prevent the passage of undissolved medicament from the dry compartment.

13 Claims, 3 Drawing Sheets

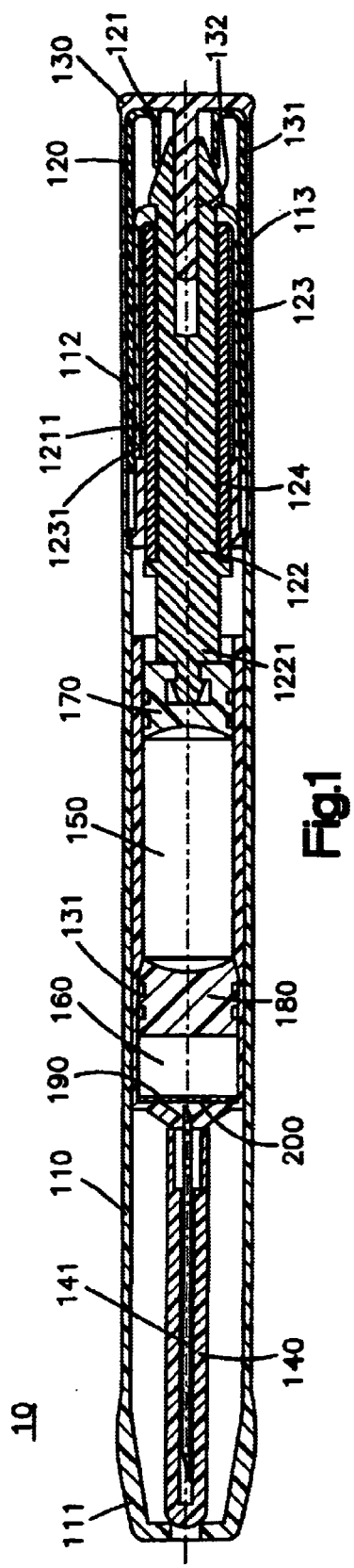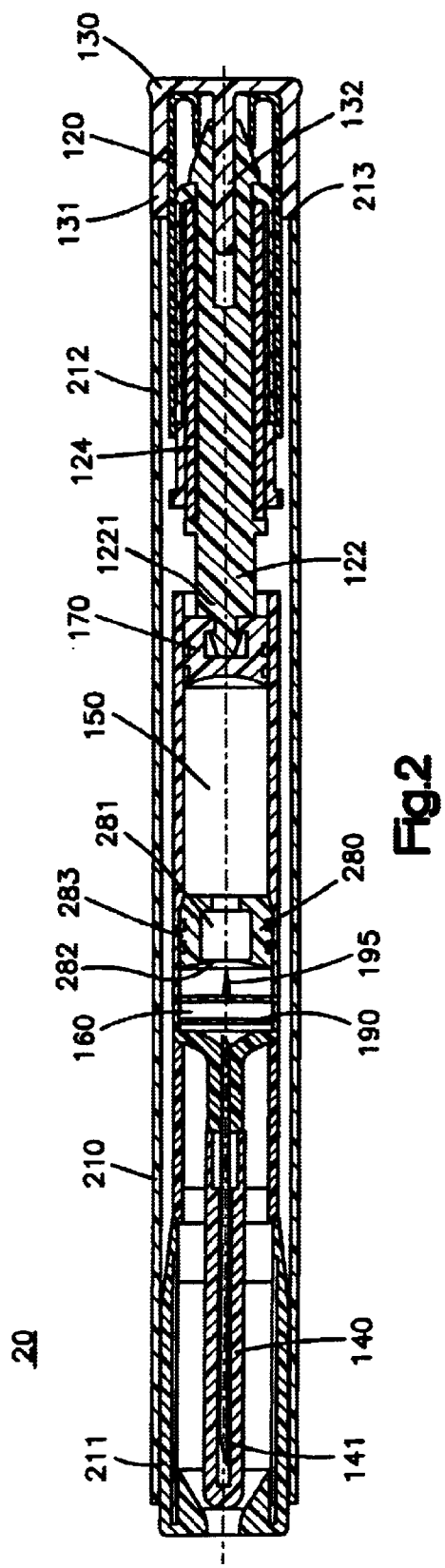

WET/DRY AUTOMATIC INJECTOR ASSEMBLY

CROSS REFERENCE TO RELATED APPLICATION

This application claims priority from U.S. Provisional Ser. No. 60/238,448, filed Oct. 10, 2000, and is incorporated herein in its entirety by reference.

FIELD OF THE INVENTION

The present invention relates to automatic injectors for delivering medicament to an injection site. In particular, the present invention is directed to an automatic injector assembly for quickly combining a liquid material with a dry material to form a liquid medicament for delivering the medicament to an injection site. In accordance with the present invention, the automatic injector assembly includes a dry medicament support structure that prevents blockage of the needle.

BACKGROUND OF THE INVENTION

An automatic injector is a device for enabling an individual to self-administer a dosage of medicament into his or her flesh. The medicament is usually stored in liquid form. The advantage of automatic injectors is that they contain a measured dosage of a liquid medicament in a sealed sterile cartridge and can be utilized for delivering the medicament into the flesh during emergency situations. Another advantage of automatic injectors is that the self-administration of the medicament is accomplished without the user initially seeing the hypodermic needle through which the medicament is delivered and without having the user to manually force the needle into his or her own flesh.

There are drawbacks associated with the storage of medicament in liquid form. Some medicaments are not stable in liquid form. Furthermore, some liquid medicaments typically have a shorter shelf life than their solid counterparts. Others have developed automatic injectors that store the medicament in solid form and a liquid injection solution. These injectors, disclosed for example in U.S. Pat. No. 35,986, entitled "Multiple Chamber Automatic Injector," (the disclosure of which is incorporated herein specifically by reference), however, require the user of the injector to expedite dissolution of the solid component by manually shaking the liquid component and the solid component immediately prior to injection. This increases the time needed to administer a dose of medicament. Furthermore, the improper mixing of the medicament with the liquid injection solution may release an insufficient dose of medicament. There is a need for an automatic injector that stores medicament in solid form that does not require manual premixing by the user. Furthermore, rapid delivery of the medicament is needed for emergency medical situations (e.g. nerve gas and chemical agent poisoning).

OBJECTS OF THE INVENTION

It is therefore an object of the present invention to provide an automatic injector device that stores medicament in a solid form for increased shelf life.

It is another object of the present invention to provide an automatic injector device that automatically mixes a solid medicament with a liquid injection solution upon activation.

It is another object of the present invention to provide an automatic injector device that provides at least one medicament support that prevents the passage of undissolved medicament to the needle assembly of the injector device.

It is another object of the present invention to provide an automatic injector device that pressurizes the liquid injection solution upon activation of the injector device.

Additional objects and advantages of the invention are set forth, in part, in the description which follows, and, in part, will be apparent to one of ordinary skill in the art from the description and/or practice of the invention.

SUMMARY OF THE INVENTION

In response to the foregoing challenges, applicants have developed an innovative automatic injection device having both wet and dry storage compartments. The present invention is directed to an automatic injection device containing a pre-loaded charge of medicament for automatically self-administering the medicament upon actuation thereof. The operation of the automatic injector requires no shaking by the user. The automatic injection device includes a housing assembly having an interior chamber, an activation assembly and a needle assembly for dispensing a dissolved medicament to a user. A dry compartment for storing a predetermined dry charge of dry medicament is located within the interior chamber. A wet compartment for storing a predetermined amount of liquid injection solution is also located within the interior chamber. A separation assembly separates the dry compartment from the wet compartment. The separation assembly prevents transfer of the liquid injection solution from the wet compartment to the dry compartment prior to activation of the automatic injection device.

The injection device may further include one or more medicament support assemblies located within the dry compartment. In accordance with the present invention, each medicament support assembly prevents the passage of undissolved medicament from the dry compartment. Preferably, each medicament support assembly includes a plurality of apertures formed therein, which are sized to prevent passage of the undissolved medicament.

BRIEF DESCRIPTION OF THE DRAWINGS

The invention will be described in conjunction with the following drawing in which like reference numerals designate like elements and wherein:

FIG. 1 is a cross-sectional side view of a wet/dry automatic injector assembly in accordance with a first embodiment of the present invention;

FIG. 2 is a cross-sectional side view of a wet/dry automatic injector assembly in accordance with a second embodiment of the present invention;

DETAILED DESCRIPTION OF THE INVENTION

Figure 3:
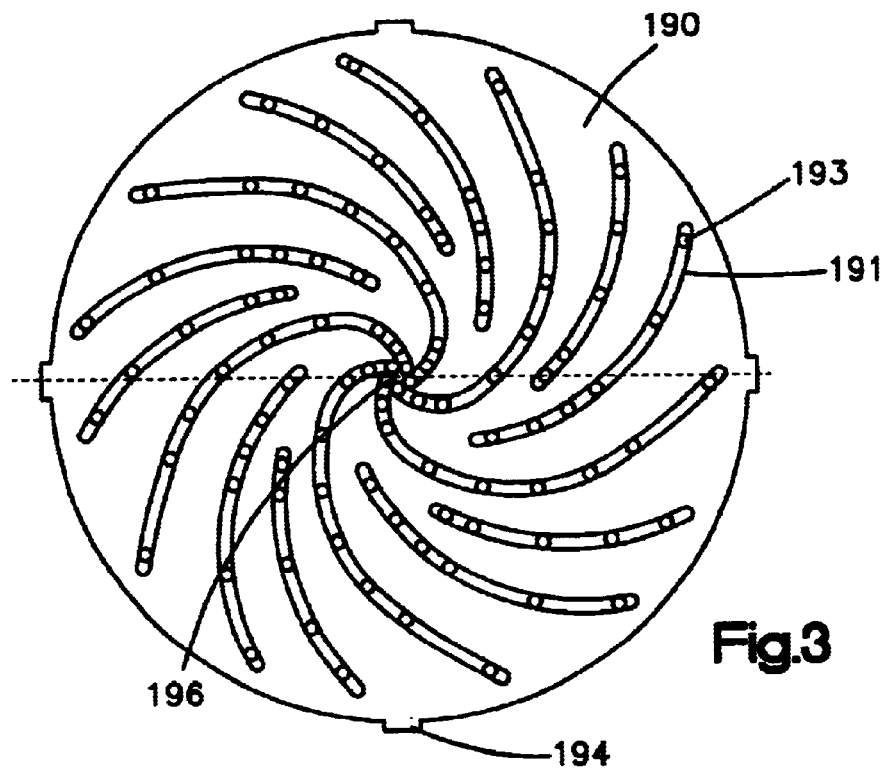
FIG. 3 is an overhead view of a medicament support for the wet/dry automatic injector assembly of the present invention.

The present invention is described in connection with a push button type auto injector, whereby the user removes an end cap assembly and presses a button to trigger the injection process. The present invention, however, is not limited to push button type automatic injectors; rather, it is contemplated that the present invention may be incorporated into a nose activated auto injector, as described for example in U.S. Pat. No. 5,658,259. The disclosures of which are hereby specifically incorporated herein by reference. It is contemplated that the present invention may be employed in a syringe.

An automatic injector assembly 10 according to a first embodiment of the present invention is illustrated in FIG. 1. The automatic injector assembly 10 includes a generally hollow housing 110. The housing 110 includes an injection insertion end 111 and an activation end 112. An actuator assembly 120 extends from an opening 113 in the activation end 112 of the housing 110. The actuator assembly 120 is slidably received within the housing 110. A removable end cap assembly 130 is releasably secured to the actuator assembly 120. When the end cap assembly 130 is secured to the actuator assembly 120, a side portion 131 of the end cap assembly 130 is adapted to abut the housing 110 to prevent movement of the actuator assembly 120 and unintentional injection of the medicament.

The actuator assembly or activation assembly 120 includes a push button actuator assembly 121 having a hollow interior. The end cap assembly 130 engages the push button actuator assembly 121. A collet 122 is located within the hollow interior of the push button actuator assembly 121. An inner tube 123 is also located within the hollow interior of the push button actuator assembly 121. The inner tube 123 is adapted to contact the collet 122, as shown in FIGS. 1 and 2. An opposite end of the inner tube 123 may include an engagement rib 1231 that is adapted to be received within a complementary recess 1211 within the push button actuator assembly 121. A drive assembly 124 is positioned within a space formed between the collet 122 and the inner tube 123. A pin 132 extends from the end cap assembly 130 and is received within the collet 122 to prevent or block the collet 122 from collapsing prior to activation.

The user removes the end cap assembly 130. The pin 132 no longer prevents movement of the collet 122. Upon depression of the actuator assembly 121, the drive assembly 124 provides the necessary force when activated to operate the injector to inject the user with a necessary dosage of medicament. It is contemplated that the drive assembly 124 may be a spring assembly, a compressed gas assembly or any other suitable energy storing device. When activated, the drive assembly 124 causes the collet 122 to move such that a needle assembly 140 extends from an opening in the injection end 111 of the housing 110. Movement of the collet 122 also causes mixing of the dry medicament with the liquid injection solution, described in greater detail below.

One end 1221 of the collet 122 extends into a wet container 150 located within the housing 110 for holding the liquid injection solution. The end 1221 of the collet 122 is adapted to contact a first plunger assembly 170 located within the wet container 150. The first plunger assembly 170 is adapted to engage the side wall of the wet container 150 to prevent leakage of the contents (e.g. liquid injection solution) of the wet container 150 from the activation end 112 of the housing 110. The first plunger assembly 170 is preferably formed from a material having low frictional properties such that the collet 122 and first plunger assembly 170 may easily slide within the wet container 150 when operated. Alternatively, the first plunger assembly 170 may be lubricated with silicon or other suitable non reactive lubricant. The movement of the collet 122 and the first plunger assembly 170 pressurizes the liquid located within the wet container 150. A suitable medicament is located within a dry container 160.

A second plunger assembly or separation assembly 180 forms a barrier between the wet compartment 150 and the dry compartment 160. The second plunger assembly 180 prevents mixing of the dry medicament and liquid injection solution prior to activation of the automatic injector assembly. The second plunger assembly 180 is adapted to engage the side wall of the wet container 150 to prevent passage of the contents (e.g. liquid injection solution) of the wet container 150 into the dry compartment 160 prior to activation of the automatic injection assembly. The second plunger assembly 180 is preferably formed from a material having low frictional properties such that the second plunger assembly 180 may easily slide when operated. Alternatively, the second plunger assembly 180 may be lubricated with silicon or other suitable non reactive lubricant. The movement of the second plunger assembly 180 opens the fluid passage between the wet compartment and the dry compartment 160.

During operation, the actuator assembly 120 releases the collet 122, which applies pressure on the first plunger assembly 170. The application of pressure on the first plunger assembly 170 by the collet and spring assembly 124 moves the first plunger assembly 170 in the direction of the needle assembly 140. This pressurizes the liquid injection solution located within the wet compartment 150. The increased pressure within the wet compartment 150 moves the second plunger assembly 180 towards the needle assembly 140. This movement of the second plunger assembly 180 opens a fluid passageway 181 between the wet compartment 150 and the dry compartment 160. There is no compression of the dry medicament. The fluid passageway 181 may include recesses formed in the sidewall of the wet compartment 150 and the dry compartment 160, which open upon a predetermined movement of the second plunger assembly 180. It is contemplated that the fluid passageway 181 may be formed by a reduced fit between the wet compartment 150 and the second plunger assembly 180, a series of by-pass slots, changes in diameter in the compartments 150 and 160, ribs on the container that distort the second plunger assembly or any other assembly that is capable of permitting that permit the flow of liquid injection solution around the second plunger assembly 180.

As the first plunger assembly 170 moves in the direction of the needle assembly 140, the liquid injection solution is transferred from the wet compartment 150 to the dry compartment where it mixes with and dissolves the dry medicament. The mixture of dissolved dry medicament and the liquid injection solution is then transferred to the needle assembly 140 where it is injected into the user through needle 141. To prevent the passage of undissolved dry medicament to the needle assembly 140, a medicament support 190 is provided adjacent the end of the dry compartment 160 adjacent the needle assembly 140. The support 190 prevents blockage of the needle assembly 141 with dry medicament. The support 190 prevents the dry medicament from entering the area surrounding the needle assembly 140 while permitting passage of the mixture of dissolved medicament and liquid injection solution. The support 190 will be described in greater detail below. It is contemplated that multiple supports 190 may be located within the dry compartent 160. The provision of the supports 190 improves the laminar flow of the liquid injection solution through the dry medicament.

A diaphragm assembly 200 may also be provided adjacent the medicament support 190. The diaphragm assembly 200 prevents the passage of the liquid injection solution to the needle assembly 140 prior to activation of the actuator assembly 120. The diaphragm assembly 200 does not rupture until sufficient pressure builds up whereby either the butt end of the needle assembly 140 or pressure build up rupture the diaphragm.

An automatic injector assembly 20 according to a second embodiment of the present invention is illustrated in FIG. 1. The automatic injector assembly 20 includes a generally hollow housing 210. The housing 210 includes an injection insertion end located at nose cone assembly 211 and an activation end 212. Like the embodiment described above, an actuator assembly 120 extends from an opening 213 in the activation end 212 of the housing 210. The actuator assembly 120 is slidably received within the housing 110. A removable end cap assembly 130 is releasably secured to the actuator assembly 120. When the end cap assembly 130 is secured to the actuator assembly 120, a side portion 131 of the end cap assembly 130 is adapted to abut the housing 110 to prevent movement of the actuator assembly 120 and unintentional injection of the medicament.

The drive assembly 124 provides the necessary force when activated to operate the injector assembly 20 to inject the user with a necessary dosage of medicament. When activated, the drive assembly 124 causes the collet 122 to move such that a needle assembly 140 extends from an opening in the nose cone assembly 211 of the housing 210.

One end 1221 of the collet 122 extends into a wet container 150 located within the housing 210 for holding the liquid injection solution. The end 1221 of the collet 122 is adapted to contact a first plunger assembly 170 located within the wet container 150. The first plunger assembly 170 is adapted to engage the side wall of the wet container 150 to prevent leakage of the contents (e.g. liquid injection solution) of the wet container 150 from the activation end 212 of the housing 210.

A second plunger assembly or separation assembly 280 forms a barrier between the wet compartment 150 and a dry compartment 160. The second plunger assembly 280 is adapted to engage the side wall of the wet container 150 to prevent passage of the contents (e.g. liquid injection solution) of the wet container 150 into the dry compartment 160 prior to activation of the automatic injection assembly.

The second plunger assembly 280 includes a central cavity 281. One end of the cavity 281 is open into the wet container 150. An opposite end of the cavity is covered with a membrane assembly 282. The membrane assembly 282 provides a barrier between the wet compartment 150 and the dry compartment 160. Upon rupture of the membrane assembly 282, the liquid injection solution travels from the wet compartment 150 through the cavity 281 into the dry compartment 160. It is contemplated that the membrane assembly 282 may rupture either by a build up of pressure within the wet compartment 150 due to the movement of the first plunger assembly 170 or by contacting a projection or spike on medicament support, described below.

The dry medicament located within the dry compartment 160 may be located between a pair of medicament supports 190. The supports 190 prevent the passage of undissolved dry medicament to the needle assembly 140 and the wet compartment 150. The supports 190 are described in greater detail below.

During operation, the spring assembly 124 releases the collet 122, which applies pressure on the first plunger assembly 170. The application of pressure on the first plunger assembly 170 moves the first plunger assembly 170 in the direction of the needle assembly 140. This pressurizes the liquid injection solution located within the wet compartment 150. The increased pressure within the wet compartment 150 moves the second plunger assembly 280 towards the needle assembly 140. The membrane 282 is ruptured when it contacts a projection 195 on one of the supports 190, as shown in FIG. 2. The liquid injection solution then flows through the cavity 281 to the dry compartment 160. The movement of the second plunger assembly 280 may also open at least one by-pass passageway 283 in the sidewall of the housing 210. The liquid injection solution mixes and dissolves with the dry medicament in the dry compartment 160. The mixture passes through the support 190 adjacent the needle assembly 140.

Figure 4:
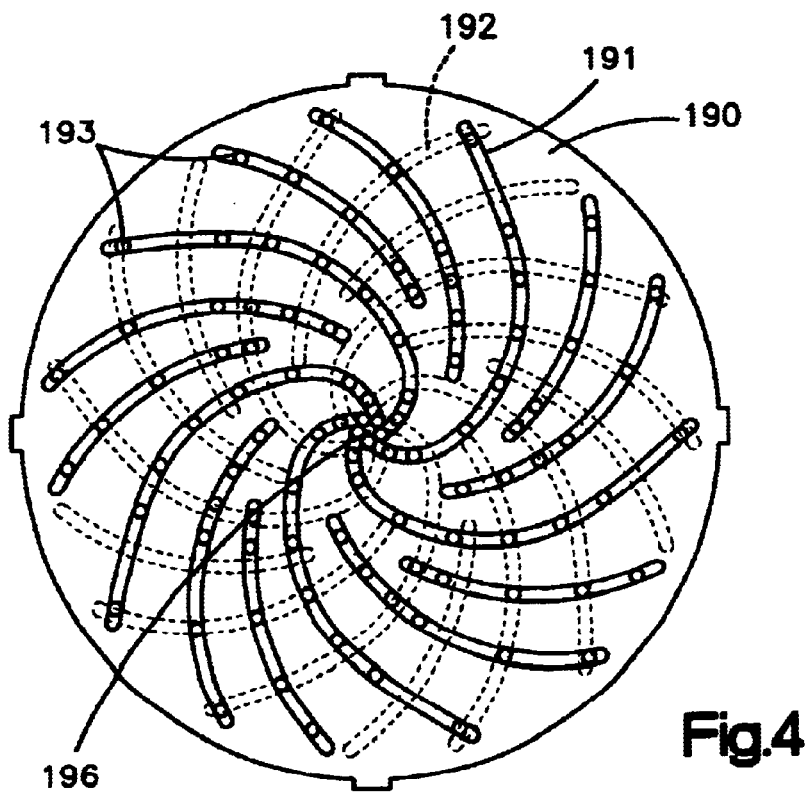
FIG. 4 is an overhead view of the medicament support of FIG. 3 illustrating the overlay of grooves on the medicament support to form an array of apertures.

The structure of the supports 190 will now be described in connection with FIGS. 3–8. Each support 190 is preferably formed from a single plate. The plate includes a plurality of openings or grooves 191 and 192 formed therein, as shown in FIGS. 3 and 4. The grooves 191 and 192 are formed on opposite sides of the plate. The intersection of the grooves 191 and 192 form apertures 193. Each aperture 193 extends through the support 190 such that the liquid injection solution and the dissolved medicament may pass there through. The grooves 191 and 192, as shown, have an arcuate shape. The present invention, however, is not limited to this configuration; rather, it is contemplated that any shaped groove may employed provided the grooves on one plate selectively overlap with the grooves on the other plate to form the above-described openings. The supports 190 may are provided with one or more tabs 194 extending from the perimeter of the plates. The optional tabs 194 are adapted to be received within complementary grooves, not shown, formed on the interior wall of the dry compartment 160 to maintain the lateral orientation of the supports 190 within the compartment 160. It is contemplated that the supports 190 may be formed from plastic, metal or any other suitable material provided the material does not react with the dry medicament during storage. The grooves 191 and 192 may be formed by machining, photo-etching, molding or any other suitable means. Additionally, it is contemplated that the apertures 193 may be formed without the use of the grooves 191 and 192; rather, the apertures 193 may be formed by machining, photo-etching, molding or any other suitable means.

Figure 5:
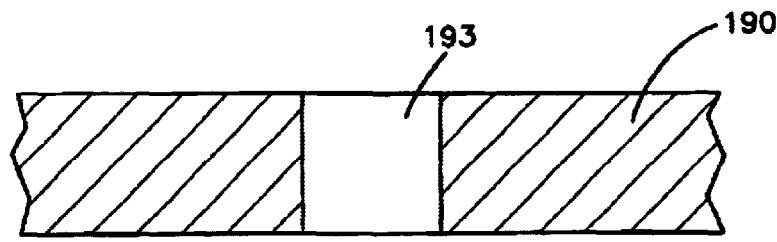
FIGS. 5–8 are various cross-sectional views illustrating various aperture configurations for the medicament support of FIGS. 3 and 4.
Figure 6:
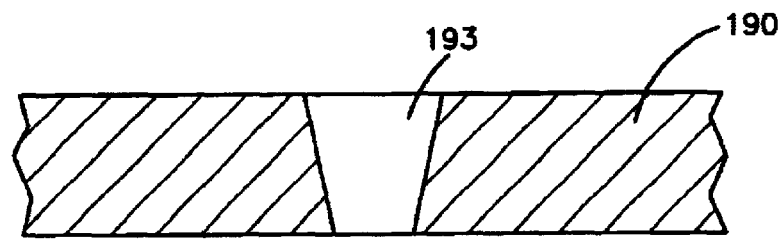
Figure 7:
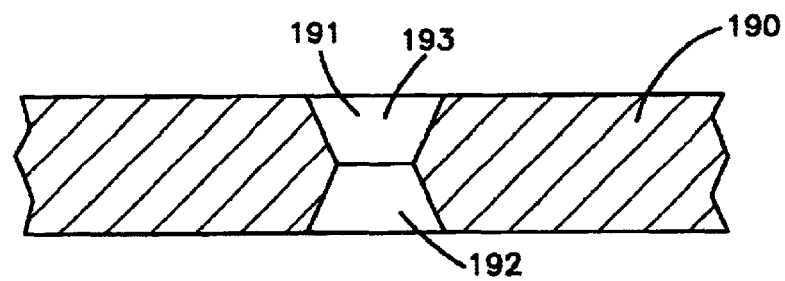
Figure 8:
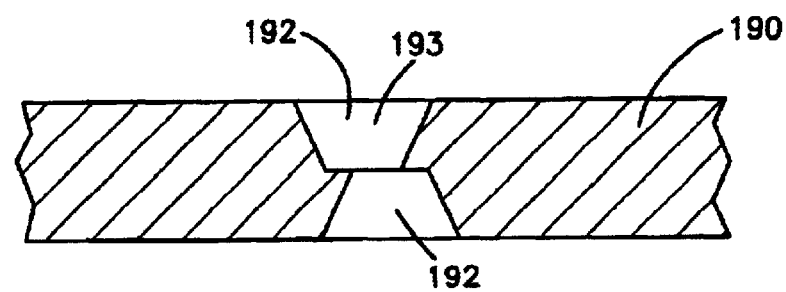
Figure 9:
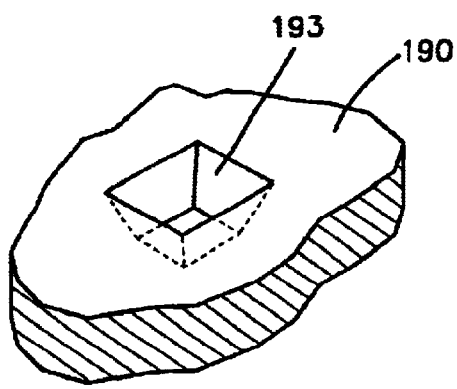
FIGS. 9 and 10 are cross-sectional views illustrating the shape and taper of various aperture configurations for the medicament support of FIGS. 3 and 4.
Figure 10:
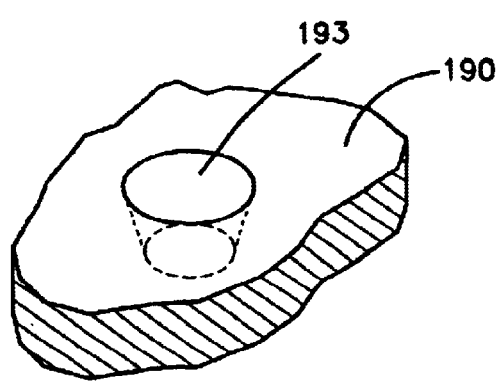

The dimensions and cross-sectional shape of the apertures 193 may vary. It is preferable that the apertures 193 be sized and shaped to prevent the passage of dry medicament there through. The apertures 193 in the medicament support 190 may be of such a shape so that the dry medicament fills and blocks the aperture to prevent the passage of the dry medicament prior to being dissolved by the liquid injection solution. The dry medicament enters the aperture and becomes compacted in the aperture due to the restriction in the cross-sectional area of the aperture, which clogs and closes the aperture until it is opened by the liquid injection solution. The apertures need not have a particular cross sectional shape. The apertures may be circular or square, as shown, for example, in FIGS. 9 and 10. The apertures may have a gradual taper, as shown in FIG. 6, a taper that varies, as shown in FIG. 7 or an offset taper, as shown in FIG. 8. Any configuration is contemplated so long as the dry medicament is prevented from passing through the support. Numerous shapes and configurations are contemplated, as shown for example, in FIGS. 5–8. In FIG. 5, the aperture 193 is sized to prevent the passage of undissolved medicament. The apertures 193 in FIGS. 6–8 are sized and shaped to trap the undissolved medicament. The supports 190 may also include a central aperture 196. Although the supports 190, as described herein, are formed from a single plate, it is contemplated that the supports can be formed a pair of plates 191 and 192.

It will be apparent to those skilled in the art that various modifications and variations may be made without departing from the scope of the present invention. For example, it is contemplated that a cover assembly, described for example in U.S. Pat. No. 5,295,965 (the disclosure of which is specifically incorporated herein by reference) may be secured to the injection end of the housing 110 after deployment of the medicament. Furthermore, the automatic injector may further include a nipple plunger assembly, as described for example in U.S. Pat. No. 5,465,727 (the disclosure of which is specifically incorporated herein by reference). Thus, it is intended that the present invention covers the modifications and variations of the invention, provided they come within the scope of the appended claims and their equivalents.

What is claimed is:

1. An automatic injection device containing a pre-loaded charge of medicament for automatically sell dminisiering the medicameni upon actuation thereof, the automatic injection device comprising:
    a housing assembly having an interior chamber, wherein the interior chamber includes, a dry compartment for storing a predetermined dry charge of dry medication therein, and a wet compartment for storing a predetermined amount of liquid injection solution therein;
    at least one medicament support assembly located within the dry compartment, wherein each medicament support assembly includes a plurality of apertures formed therein;
    a movable separation assembly located within the interior chamber for separating the dry compartment front the wet compartment, wherein the separation assembly is movable with respect to at least the dry compartment, wherein the separation assembly prevents transfer of the liquid injection solution from the wet compartment to the dry compartment prior to activation of the automatic injection device;
    an activation assembly for causing the liquid injection solution in the wet compartment to be transterred to the dry compartment, wherein the dry medicament dissolves in the liquid injection solution as the liquid injection solution passes through the dry compartment, wherein the activation assembly includes a drive assembly having a stored source of energy located therein, whereby upon actuation of the activation assembly, the drive assembly releases the stored source or energy for causing liquid injection solution in the Wet compartment to be transferred to the dry compartment; and
    a needle assembly for dispensing the liquid injection solution containing the dry medicament dissolved therein.

2. The automatic injection device according to claim 1, wherein each of the at least one medicament support assembly prevents the passage of undissolved medicament from the dry compartment.

3. The automatic injection device according to claim 2, wherein each of the apertures is sized to prevent passage of the undissolved medicament.

4. The automatic injection device according to claim 1, wherein each of the at least one medicament support assembly includes at least one support plate having the plurality of apertures formed therein.

5. An injection device containing a pre-loaded charge of medicament for self-administering the medicament upon actuation thereof, the injection device comprising:
    a housing assembly having an interior chamber, wherein the interior chamber includes a dry compartment for storing a predetermined dry charge of dry medicament therein, and a wet compartment for storing a predetermined amount of liquid injection solution therein;
    at least one medicament support assembly located within the dry compartment, wherein the at least one medicament support assembly preventing the passage of undissolved dry medicament therethrough;
    a movable separation assembly located within the interior chamber for separating the dry compartment from the wet compartment, wherein the separation assembly is movable with respect to at least the dry compartment, wherein the separation assembly prevents transfer of the liquid injection solution from the wet compartment to the dry compartment prior to activation of the automatic injection device;
    an activation assembly for causing the liquid injection solution in the wet compartment to be transferred to the dry compartment, wherein the dry medicament dissolves in the liquid injection solution as the liquid injection solution passes through the dry compartment; and
    a needle assembly for dispensing the liquid injection solution containing the dry medicament dissolved therein,
    wherein the at least one medicament support assembly includes a first medicament support located adjacent the separation assembly, and a second medicament support located adjacent the needle assembly, wherein at least one medicament support assembly includes a plurity of apertures formed therein.

6. The injection device according to claim 5, wherein the first medicament support includes at least one projection adapted to engage to the separation assembly to open a passage therein to permit the passage of the liquid injection solution from the wet compartment to the dry compartment.

7. The injection device according to claim 6, wherein the separation assembly includes a membrane assembly positioned adjacent the first medicament support, wherein at least one projection adapted to rupture the membrane assembly.

8. The injection device according to claim 5, further comprising:
    a membrane assembly positioned adjacent the second medicament support.

9. The injection device according to claim 5, wherein each of the apertures is sized to prevent passage of the undissolved medicament.

10. The injection device according to claim 3, wherein each of the at least one medicament support assembly include at least one Support plate having a plurality of apertures formed therein.

11. An injection device containing a pre-loaded charge of medicament for self-administering the medicament upon actuation thereof the injection device comprising:
    a housing assembly having an interior chamber, wherein the interior chamber includes a dry compartment for storing a predetermined dry charge of dry medicament therein, and a wet compartment for storing a predetermined amount of liquid injection solution therein;
    at least one medicament support assembly located within the dry compartment, wherein the at least one medicament support assembly preventing the passage of undissolved medicament therethrough, wherein each medicament support assembly includes a plurality of apertures formed therein;

a movable separation assembly located within the interior chamber for separating the dry compartment from the wet compartment, wherein the separation assembly is movable with respect to the dry compartment and the wet compartment, wherein the separation assembly prevents transfer of the liquid injection solution from the wet compartment to the dry compartment prior to activation of the automatic injection device;

an activation assembly for causing the liquid injection solution in the wet compartment to be transferred to the dry compartment, wherein the dry medicament dissolves in the liquid injection solution as the liquid injection solution passes through the dry compartment;

needle assembly for dispensing the liquid injection solution containing the dry medicament dissolved therein; and a diaphragm assembly positioned near one of the at least one medicament support assembly and the needle assembly.

12. The injection device according to claim 11, wherein each off the apertures is sized to prevent passage of the undissolved medicament.

13. The injection device according to claim 11, wherein each of the at least one medicament support assembly includes at least one support plate having the plurality of apertures formed therein.

* * * * *

UNITED STATES PATENT AND TRADEMARK OFFICE
CERTIFICATE OF CORRECTION

PATENT NO. : 6,953,445 B2
DATED : October 11, 2005
INVENTOR(S) : John G. Wilmot et al.

It is certified that error appears in the above-identified patent and that said Letters Patent is hereby corrected as shown below:

Column 7,
Line 21, change "sell dminisiering" to -- self-administering --;
Line 22, change "medicameni" to -- medicament --;
Line 25, delete the comma between "includes" and "a dry";
Line 26, change "medication" to -- medicament --;
Line 34, change "front" to -- from --;
Line 43, change "transterred" to -- transferred --;
Line 51, change "or" to -- of --; and
Line 52, change "Wet" to -- wet --.

Column 8,
Line 27, change "dispencing" to -- dispensing --;
Line 35, change "plurity" to -- plurality --;
Line 54, change "claim 3" to -- claim 5 --;
Line 56, change "include" to -- includes -- and "Support" to -- support --;
Line 60, insert a comma between "thereof" and "the".

Column 10,
Line 1, insert -- a -- before "needle"; and
Line 9, change "off" to -- of --.

Signed and Sealed this

Eighteenth Day of April, 2006

JON W. DUDAS
*Director of the United States Patent and Trademark Office*